United States Patent [19]

Harris

[11] Patent Number: 4,926,845
[45] Date of Patent: May 22, 1990

[54] SACRUM SUPPORT DEVICE

[76] Inventor: Don W. Harris, P.O. Box 3490, Ft. Stewart, Ga. 31314

[21] Appl. No.: 248,981

[22] Filed: Sep. 26, 1988

[51] Int. Cl.⁵ .............................................. A61F 5/24
[52] U.S. Cl. ..................................... 128/78; 128/98.1; 128/168; 128/876
[58] Field of Search ................. 2/44, 400; 128/75, 78, 128/87, 96.1, 98.1, 158, 168, 876, 882

[56] References Cited

U.S. PATENT DOCUMENTS

| | | | |
|---|---|---|---|
| 623,315 | 4/1899 | Kennedy | 128/161 |
| 930,031 | 8/1909 | Bierhoff | 128/158 |
| 976,564 | 11/1910 | Goodson | 128/876 X |
| 1,008,500 | 11/1911 | Thornton | 2/44 |
| 1,722,192 | 7/1929 | Brokaw | 2/44 |
| 2,282,021 | 5/1942 | Berringfield | 128/96.1 |
| 2,427,428 | 9/1947 | Vitale | 128/158 |
| 2,543,095 | 2/1951 | Davis | 128/96.1 |
| 2,593,262 | 4/1952 | Calabrese | 128/96.1 |
| 2,615,445 | 10/1952 | Holmes | 128/168 |
| 2,843,116 | 7/1958 | Grannan | 128/78 |
| 3,116,736 | 1/1964 | Alberts | 128/96.1 |
| 3,171,409 | 3/1965 | Cetrone | 128/96.1 |
| 3,294,086 | 12/1966 | Nelkin | 128/96.1 |
| 3,888,245 | 6/1975 | Berntson et al. | 128/78 |
| 3,909,847 | 10/1975 | Holt et al. | 128/168 |
| 4,014,044 | 3/1977 | Figueroa et al. | 128/98.1 |
| 4,709,692 | 12/1987 | Kirschenberg | 128/78 |

Primary Examiner—Robert A. Hafer
Assistant Examiner—Kevin G. Rooney
Attorney, Agent, or Firm—Jerry T. Kearns

[57] ABSTRACT

A sacrum support device for use by individuals when performing sit-up exercises provides a protective flexible rubber pad. In a first embodiment, the pad is supported between a waist encircling strap and a pair of leg encircling straps by two pairs of support straps. The pad has a pentagonal shape with a downwardly pointing apex and is positioned over the sacrum of the individual. In a second embodiment, briefs formed from a washable fabric material are provided with a rear pocket for insertion of the pad. The pocket and pad may have a generally triangular or rectangular shape. The device provides protection for the sacrum or tail bone which is frequently irritated by repeated sit-up exercises.

1 Claim, 3 Drawing Sheets

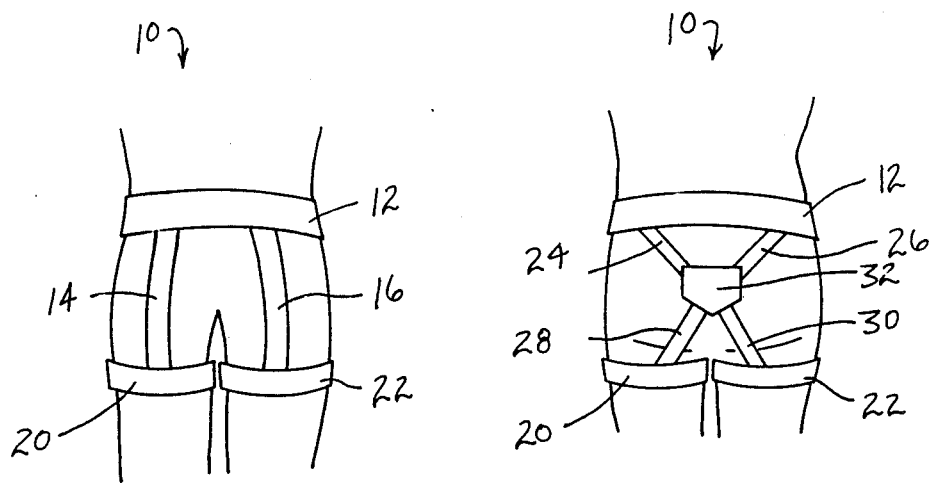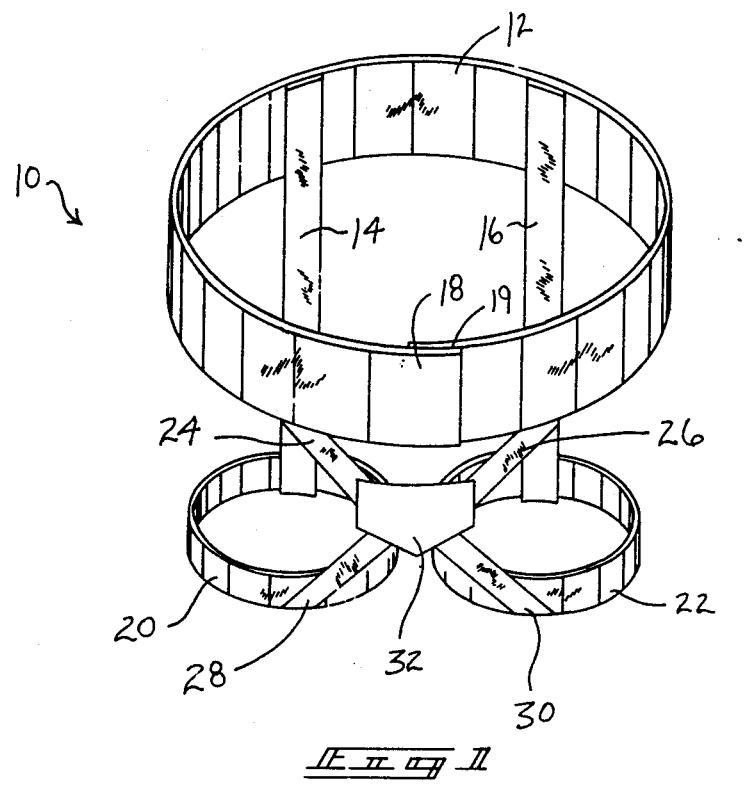

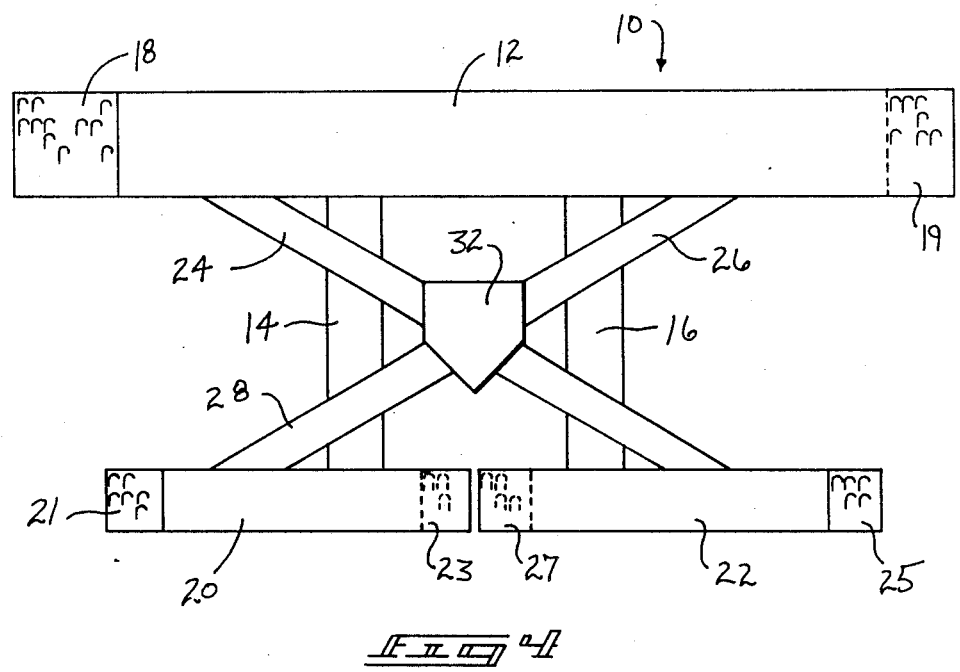
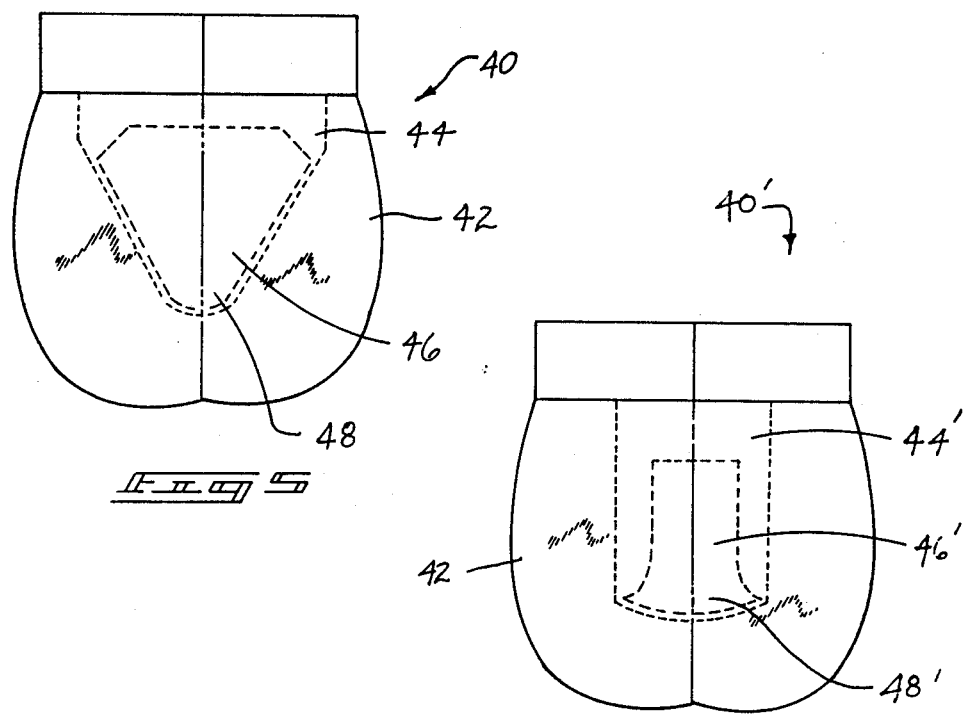

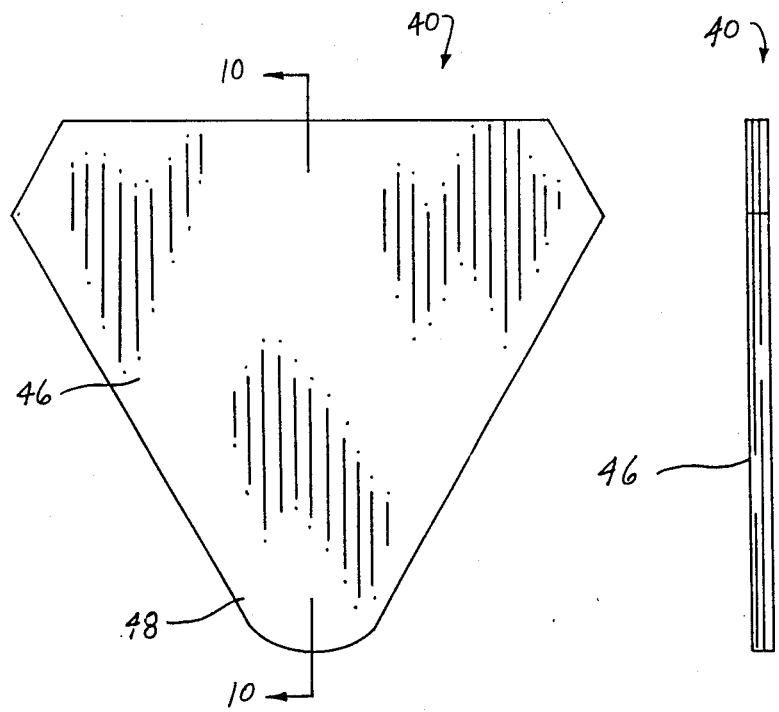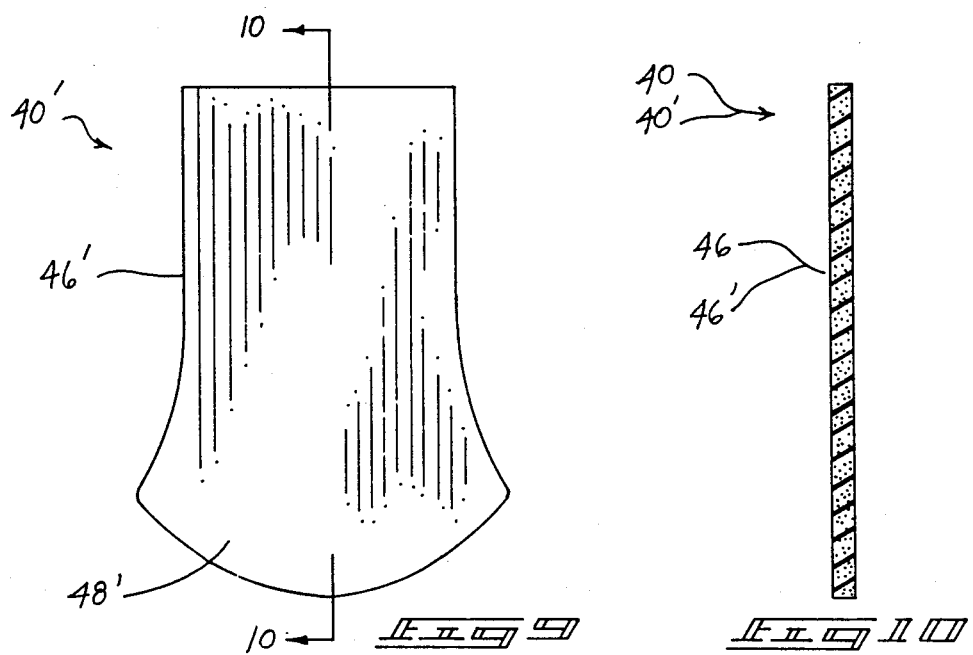

SACRUM SUPPORT DEVICE

BACKGROUND OF THE INVENTION

1. Field of the Invention

The present invention relates to support devices, and more particularly pertains to a new and improved sacrum support device for preventing pain and injury to individuals performing repeated sit-up exercises. The sacrum or tail bone for most individuals is a very tender and sensitive area which is completely unprotected by conventional sweat pants or exercise shorts. In order to overcome this problem and to enable training by both serious and casual athletes, the present invention provides two embodiments of a sacrum support and protection pad device.

2. Description of the Prior Art

Various types of support devices are known in the prior art. A typical example of such a support device is to be found in U.S. Pat. No. 2,282,021, which issued to T. Benningfield on May 5, 1942. This patent discloses an abdominal support which includes a waist encircling strap adjustably connected to a shoulder harness. U.S. Pat. No. 2,543,095, which issued to R. Davis on Feb. 27, 1951, discloses a sacroiliac waist encircling support belt. The belt is secured by adjustable strap fasteners. U.S. Pat. No. 2,593,262, which issued to J. Calabrese on Apr. 15, 1952, discloses a hernia support device which includes an irregularly shaped support pad provided with strap securement. U.S. Pat. No. 3,116,736, which issued to S. Alberts on Jan. 7, 1964, discloses a support belt arrangement for supporting certain portions of the human body for applying external pressure for the control of varicose veins and other pathological conditions. The device utilizes a waist encircling belt and is provided with a plurality of straps. U.S. Pat. No. 3,171,409, which issued to L. Cetrone on Mar. 2, 1965, discloses an orthopedic padded waist encircling belt provided with a buckle fastener.

While the above mentioned devices are suited for their intended usage, none of these devices are capable of providing support and protection to the sacrum of an individual while performing sit-up exercises. Additionally, none of the aforesaid devices disclose the use of a pentagonal shaped rubber pad suspended by two pairs of support straps between a waist encircling strap and a pair of leg encircling straps. Additional features of the present invention, not disclosed by the aforesaid prior art devices include the use of briefs formed from a washable material and provided with a rear pocket for the reception of a removable rubber sacrum support and protection pad. Inasmuch as the art is relatively crowded with respect to these various types of support devices, it can be appreciated that there is a continuing need for and interest in improvements to such support devices, and in this respect, the present invention addresses this need and interest.

SUMMARY OF THE INVENTION

In view of the foregoing disadvantages inherent in the known types of support devices now present in the prior art, the present invention provides an improved sacrum support device. As such, the general purpose of the present invention, which will be described subsequently in greater detail, is to provide a new and improved sacrum support device which has all the advantages of the prior art support devices and none of the disadvantages.

To attain this, representative embodiments of the concepts of the present invention are illustrated in the drawings and make use of a protective flexible rubber pad. In a first embodiment, the pad is supported between a waist encircling strap and a pair of leg encircling straps by two pairs of support straps. The pad has a pentagonal shape with a downwardly pointing apex and is positioned over the sacrum of the individual. In a second embodiment, briefs formed from a washable fabric material are provided with a rear pocket for insertion of the pad. The pocket and pad may have a generally triangular or rectangular shape. The device provides protection for the sacrum or tail bone which is frequently irritated by repeated sit-up exercises.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved sacrum support device which has all the advantages of the prior art support devices and none of the disadvantages.

It is another object of the present invention to provide a new and improved sacrum support device which may be easily and efficiently manufactured and marketed.

It is a further object of the present invention to provide a new and improved sacrum support device which is of a durable and reliable construction.

An even further object of the present invention is to provide a new and improved sacrum support device which is susceptible of a low cost of manufacture with regard to both materials and labor, and which accordingly is then susceptible of low prices of sale to the consuming public, thereby making such support devices economically available to the buying public.

Still yet another object of the present invention is to provide a new and improved sacrum support device which provides in the apparatuses and methods of the prior art some of the advantages thereof, while simultaneously overcoming some of the disadvantages normally associated therewith.

Still another object of the present invention is to provide a new and improved sacrum support device for use by individuals performing sit-up exercises.

Yet another object of the present invention is to provide a new and improved sacrum support device for use by individuals while performing sit-up exercises which utilizes a pentagonal shape sacrum protection pad suspended by two pairs of support straps between a waist encircling strap and a pair of leg encircling straps.

Even still another object of the present invention is to provide a new and improved sacrum support device which utilizes briefs formed from a washable fabric material provided with a rear pocket for the reception of a removable sacrum support and protection pad.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the sacrum support device according to the first embodiment of the present invention.

FIG. 2 is a front view of the sacrum support device according to the first embodiment of the present invention, as worn by an individual.

FIG. 3 is a rear view of the sacrum support device according to the first embodiment of the present invention, as worn by an individual.

FIG. 4 is a side view of the sacrum support device according to the first embodiment of the present invention, with the various attaching straps in an extended condition.

FIG. 5 is a rear view of a sacrum support device according to a second embodiment of the present invention, utilizing a triangular shaped sacrum protection pad.

FIG. 6 illustrates the triangular sacrum protection pad utilized in the second embodiment of the present invention.

FIG. 7 is a side view of the sacrum protection pad of FIG. 6.

FIG. 8 is a rear view of a slightly modified form of sacrum support device according to the second embodiment of the present invention, utilizing a generally rectangular shaped sacrum protection pad.

FIG. 9 illustrates the modified form of generally rectangular sacrum protection pad.

FIG. 10 is a cross sectional view which illustrates the padded rubber material of the sacrum protection pad as illustrated in FIGS. 6 and 9.

DESCRIPTION OF THE PREFERRED EMBODIMENT

With reference now to the drawings, and in particular to FIG. 1 thereof, a new and improved sacrum support device embodying the principles and concepts of the present invention and generally designated by the reference numeral 10 will be described.

More specifically, it will be noted that the first embodiment 10 of the invention includes a waist strap 12 having a pair of generally parallel downwardly extending support straps 14 and 16 connected respectively to leg straps 20 and 22. The waist strap 12 is adapted for securement around the waist of an individual by cooperating VELCRO fastening portions 18 and 19. Leg straps 20 and 22 are provided with similar fasteners to be subsequently described and illustrated.

A pentagonal shaped sacrum protection pad 32 is secured between the waist encircling strap 12 and leg encircling straps 20 and 22 by a first pair of pad support straps 24 and 26, connecting the upper portion of the pad 32 to a rear portion of the waist strap 12. A second pair of pad support straps 28 and 30, connect lower portions of the pad 32 to rear portions of the leg straps 20 and 22. Through this construction, the sacrum or tail bone protection pad 32 is suspended between the waist strap 12 and the leg straps 20 and 22 when worn by an individual. This positions the pad 32 over the sacrum of the individual, thus enabling the individual to perform sit-up exercises without chaffing or discomfort. Serious athletes and even amateur health enthusiasts frequently encounter irritation, bleeding and eventual scarring of the sacrum area due to repeated sit-up exercises. Through the use of the sacrum support device of the present invention, these symptoms are alleviated.

FIG. 2 provides a front view of an individual wearing the sacrum support device according to the first embodiment 10 of the present invention. The strap 12 encircles the waist of the individual and the straps 20 and 22 encircle the upper leg portions of the individual. The support straps 14 and 16 extend between a front portion of the waist strap 12 and front portions of the leg straps 20 and 22.

FIG. 3 provides a rear view which illustrates the protection pad 32 suspended between the waist strap 12 and the leg straps 20 and 22 by the pad support straps 24, 26, 28 and 30. The sacrum support device 10 according to the first embodiment of the present invention is adapted to be easily worn over conventional exercise shorts or sweat pants and may easily and quickly be installed or removed as required.

FIG. 4 illustrates the sacrum support device 10 removed from the individual, with the waist encircling strap 12 and leg encircling straps 20 and 22 in an extended condition. As described previously, the waist strap 12 is provided with cooperating VELCRO fastening portions 18 and 19. Leg straps 20 and 22 are provided with similar cooperating VELCRO fastening portions 21, 23, 27 and 25.

With reference now to FIG. 5, a sacrum support device 40 according to a second embodiment of the present invention will now be described. A pair of generally conventionally formed briefs 42, preferably made from a washable fabric material, are provided with a triangular shaped rear pocket 44 in which a triangular shaped pad 46 is removably received. The triangular tapering configuration of the pad 46 with the downwardly pointing apex 48 has been found to provide a minimum of interference to the movement of an exercising individual. When washing the briefs 42, the pad 46 may easily be removed. The triangular configuration of the pocket 44 provides a selfcentering mounting of the pad 46.

FIG. 6 illustrates the pad 46 of the sacrum support device 40 removed from the briefs 42.

FIG. 7 provides a side view of the pad 46.

In FIG. 8, a slightly modified form of the second embodiment 40' is illustrated. The briefs 42 are provided with a generally rectangular pocket 44' having a flared lower end portion. A generally rectangular pad 46' having a flared width lower end 48' is removably received within the pocket 44'.

FIG. 9 illustrates the modified form of pad 46' utilized in the modified form of the second embodiment 40' of the sacrum support device of the present invention.

FIG. 10 provides a cross sectional view which illustrates the foam rubber material of the pads 46 and 46' of the second embodiment 40 and modified form of second embodiment 40' of the sacrum support device of the present invention.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by letters patent of the United States is as follows:

1. A sacrum support device, comprising:
   a generally horizontally extending waist strap having fastening means for securement around an individual's waist;
   a pair of generally horizontally extending leg straps, each having fastening means for securement around an individual's leg;
   a pair of generally vertical support straps connecting said leg straps to a front portion of said waist strap;
   a pad formed from a soft resilient material;
   said pad having a pentagonal shape with an apex pointing downwardly, away from said waist strap;
   a first pair of diagonally extending pad support straps connecting said pad to a rear portion of said waist strap; and
   a second pair of diagonally extending pad support straps connecting said pad to rear portions of said leg straps, whereby said pad is disposed between said vertical support straps and between said waist and leg straps in a position to protect an individual's sacrum.

* * * * *